United States Patent
Chen et al.

(10) Patent No.: US 11,945,792 B2
(45) Date of Patent: Apr. 2, 2024

(54) CRYSTALLINE FORMS OF 6-(1-ACRYLOYL-PIPERIDIN-4-YL)-2-(4-PHENOXYPHENYL)N-ICOTINAMIDE

(71) Applicant: BEIJING INNOCARE PHARMA TECH CO., LTD., Beijing (CN)

(72) Inventors: Xiangyang Chen, Beijing (CN); Zuopeng Wang, Shanghai (CN); Liqin Yu, Nanjing (CN)

(73) Assignee: Beijing Innocare Pharma Tech Co., Ltd, Beijing (CN)

( * ) Notice: Subject to any disclaimer, the term of this patent is extended or adjusted under 35 U.S.C. 154(b) by 598 days.

(21) Appl. No.: 17/191,310

(22) Filed: Mar. 3, 2021

(65) Prior Publication Data

US 2021/0188801 A1    Jun. 24, 2021

Related U.S. Application Data

(63) Continuation of application No. PCT/CN2019/106433, filed on Sep. 18, 2019.

(60) Provisional application No. 62/732,994, filed on Sep. 18, 2018.

(51) Int. Cl.
    *C07D 401/04*     (2006.01)
    *A61K 31/4545*    (2006.01)

(52) U.S. Cl.
    CPC ........ *C07D 401/04* (2013.01); *A61K 31/4545* (2013.01); *C07B 2200/13* (2013.01)

(58) Field of Classification Search
    CPC .......................... C07D 401/04; C07B 2200/13
    See application file for complete search history.

(56) References Cited

U.S. PATENT DOCUMENTS 9,951,056 B2    4/2018   Chen et al.
2016/0237075 A1*   8/2016   Chen .................... C07D 213/82

FOREIGN PATENT DOCUMENTS

WO    2015/048662      4/2015
WO    2016100914 A1    6/2016
WO    2016105582 A1    6/2016

OTHER PUBLICATIONS

International Search Report for International Application No. PCT/CN2019/106433, dated Dec. 13, 2019. 4 pages.
Caira: "Crystalline Polymorphism of Organic Compounds", Topics in Current Chemistry, 1998, vol. 198, 2 pages.
Morissette, et al. "High-throughput crystallization: polymorphs, salts, co-crystals and solvates of pharmaceutical solids" Advanced Drug Delivery Reviews 56 (2004) 275-300, accepted Oct. 6, 2003, 26 pages.
Variankaval et al.: "From form to function: Crystallization of active pharmaceutical ingredients", AIChE, 2008, vol. 54(7), 7 pages.
Darío Braga, "Crystal Polymorphism and Multiple Crystal Forms", Feb. 2009, Chapter in Structure Bonding, DOI 10.1007/430_2008_7, pp. 25-50.
Rolf Hilfker "Relevance of Solid-State Properties for Pharmaceutical Products", 2006, pp. 1-19.

* cited by examiner

*Primary Examiner* — Robert H Havlin
*Assistant Examiner* — John D McAnany
(74) *Attorney, Agent, or Firm* — Perkins Coie LLP; Viola Kung

(57) ABSTRACT

The present invention relates to various crystalline forms of 6-(1-acryloylpiperidin-4-yl)-2-(4-phenoxyphenyl)nicotinamide. The present invention also relates to pharmaceutical compositions comprising the crystalline forms.

7 Claims, 8 Drawing Sheets

*: Solvents include acetone, 1,4-dioxane, EtOAc, MTBE, IPAc, n-heptane and etc.

CRYSTALLINE FORMS OF 6-(1-ACRYLOYLPIPERIDIN-4-YL)-2-(4-PHENOXYPHENYL)NICOTINAMIDE

This application is a continuation of PCT/CN2019/106433, filed Sep. 18, 2019; which claims the benefit of U.S. Provisional Application No. 62/732,994, filed Sep. 18, 2018. The contents of the above-identified applications are incorporated herein by reference in their entirety.

TECHNICAL FIELD

The present invention relates to different crystalline forms of 6-(1-acryloylpiperidin-4-yl)-2-(4-phenoxyphenyl)nicotinamide.

BACKGROUND OF THE INVENTION 6-(1-Acryloylpiperidin-4-yl)-2-(4-phenoxyphenyl)nicotinamide (Compound I) is a substituted nicotinamide inhibitor of Bruton's Tyrosine Kinase (BTK). The preparation of Compound I and its use in the treatment of cancer, inflammation, and autoimmune disease is described in WO2015/028662, which is incorporated herein by reference in its entirety.

DETAILED DESCRIPTION OF THE INVENTION

The present disclosure relates to specific crystalline forms of 6-(1-acryloylpiperidin-4-yl)-2-(4-phenoxyphenyl)nicotinamide (Compound I). The crystalline forms of Compound I have at least one advantage in stability, solubility and hygroscopicity, and they are suitable for pharmaceutical research and manufacturing.

Compound I

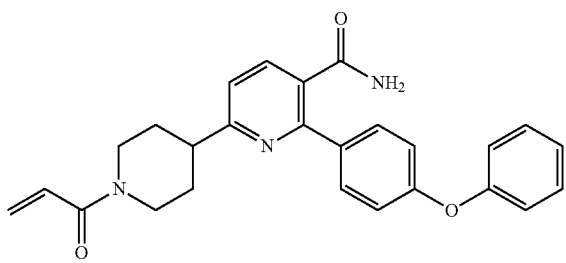

Type A Crystalline Form

Type A crystalline form is prepared from a starting material Compound I, as described in WO2015/048662. Type A crystalline form can be prepared by dissolving the starting material Compound I in dichloromethane; then precipitating with ethyl acetate.

Figure 1:
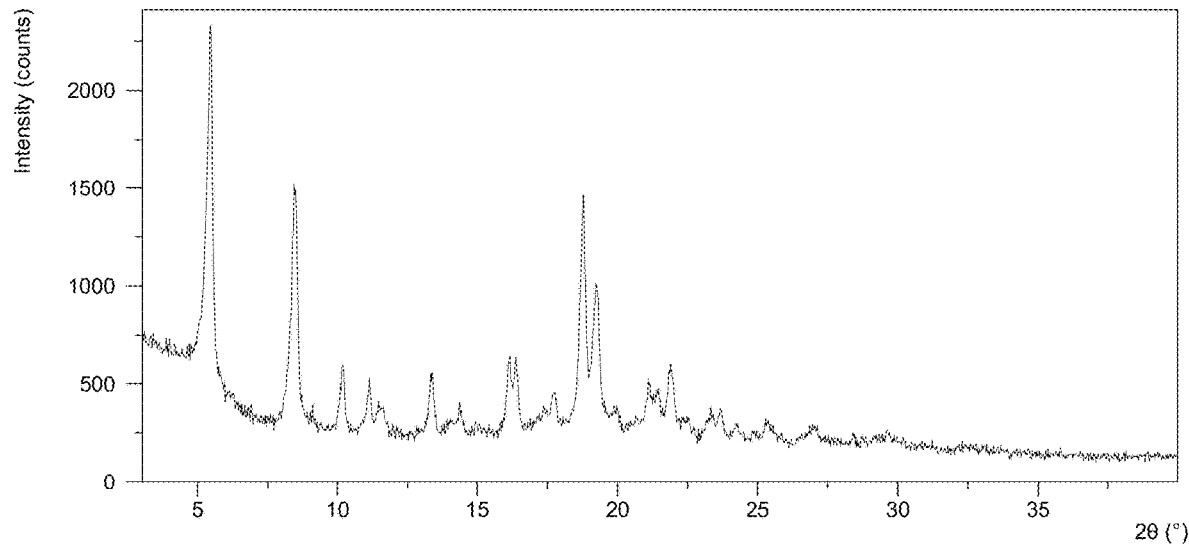
FIG. 1 shows an XRPD pattern of Type A.

The XRPD of Type A of present invention is shown in FIG. 1, which shows the most intense peaks at 2theta values of 5.4°±0.2°, 8.4°±0.2°, 18.7°±0.2°.

Furthermore, the XRPD of Type A further shows one or more characteristic peaks at 2theta values of 19.1°±0.2°, 16.1°±0.2°, 21.9°±0.2°, 10.1°±0.2°.

Furthermore, the XRPD of Type A further shows one or more characteristic peaks at 2theta values of 13.2°±0.2°, 11.1°±0.2°, 14.3°±0.2°.

The XRPD data of Type A is shown in Table 1.

TABLE 1

| 2theta | d spacing | Intensity (%) |
|---|---|---|
| 5.39 | 16.41 | 100.00 |
| 8.41 | 10.51 | 77.19 |
| 10.11 | 8.75 | 19.53 |
| 11.06 | 8.00 | 15.79 |
| 13.23 | 6.69 | 17.33 |
| 13.64 | 6.49 | 4.27 |
| 14.29 | 6.20 | 9.80 |
| 16.08 | 5.51 | 27.72 |
| 16.35 | 5.42 | 21.31 |
| 17.71 | 5.01 | 13.12 |
| 18.69 | 4.75 | 64.74 |
| 19.14 | 4.64 | 43.60 |
| 21.02 | 4.23 | 16.01 |
| 21.85 | 4.07 | 22.24 |
| 23.25 | 3.83 | 8.69 |
| 23.61 | 3.77 | 7.55 |
| 25.25 | 3.53 | 5.99 |
| 26.82 | 3.32 | 4.31 |
| 29.59 | 3.02 | 3.00 |

Type A of present disclosure is an isomorphic form, i.e. having cavities/voids in the crystal structure to allow participation of various guest molecules with appropriate size. Isomorphic forms have similar lattice structures and substantially the same XRPD pattern.

Depending on preparation conditions, such as solvent types, drying, etc., Type A may be an anhydrate, a solvate, or a hydrate. They have substantially the same XRPD patterns.

Figure 2:
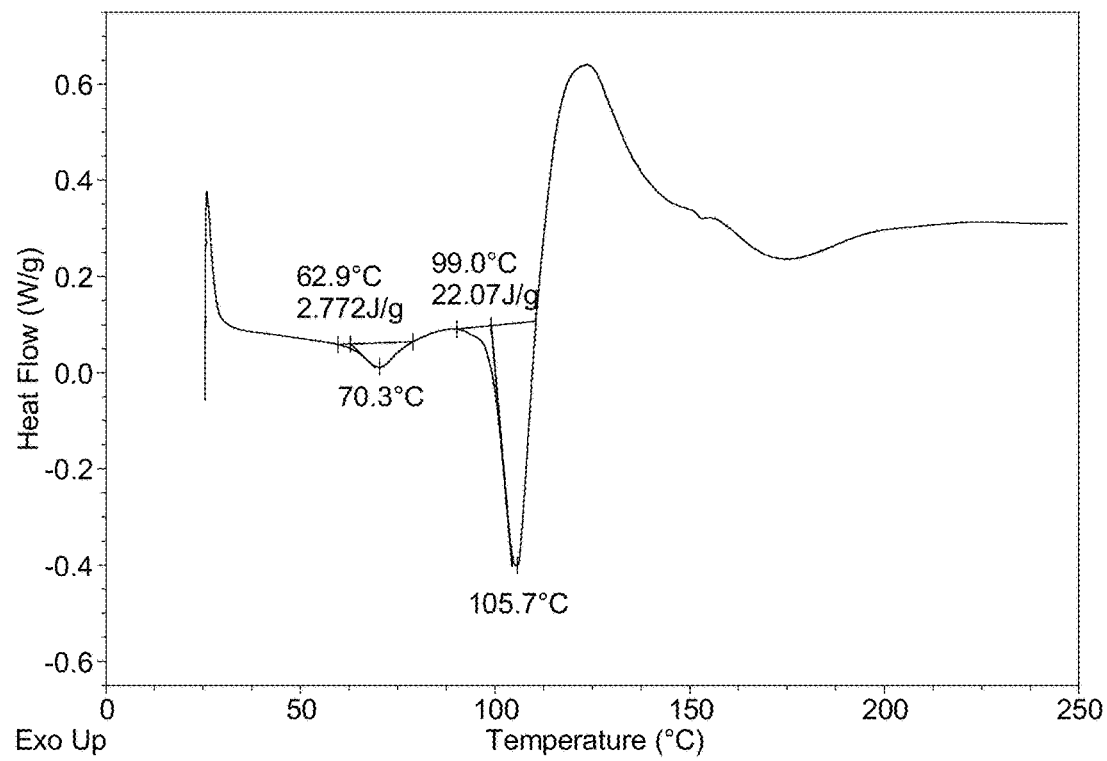
FIG. 2 shows a DSC curve of Type A in a hydrate form.

The hydrated Type A shows two endothermic peaks when heated to around 63° C. (onset temperature) and 99° C. (onset temperature); the peak temperatures are 70.3 and 105.7° C., respectively. The DSC curve is depicted in FIG. 2.

The anhydrous Type A shows one endothermic peak when heated to around 97° C. (onset temperature) with the peak temperature at 105.7° C.

Figure 3:
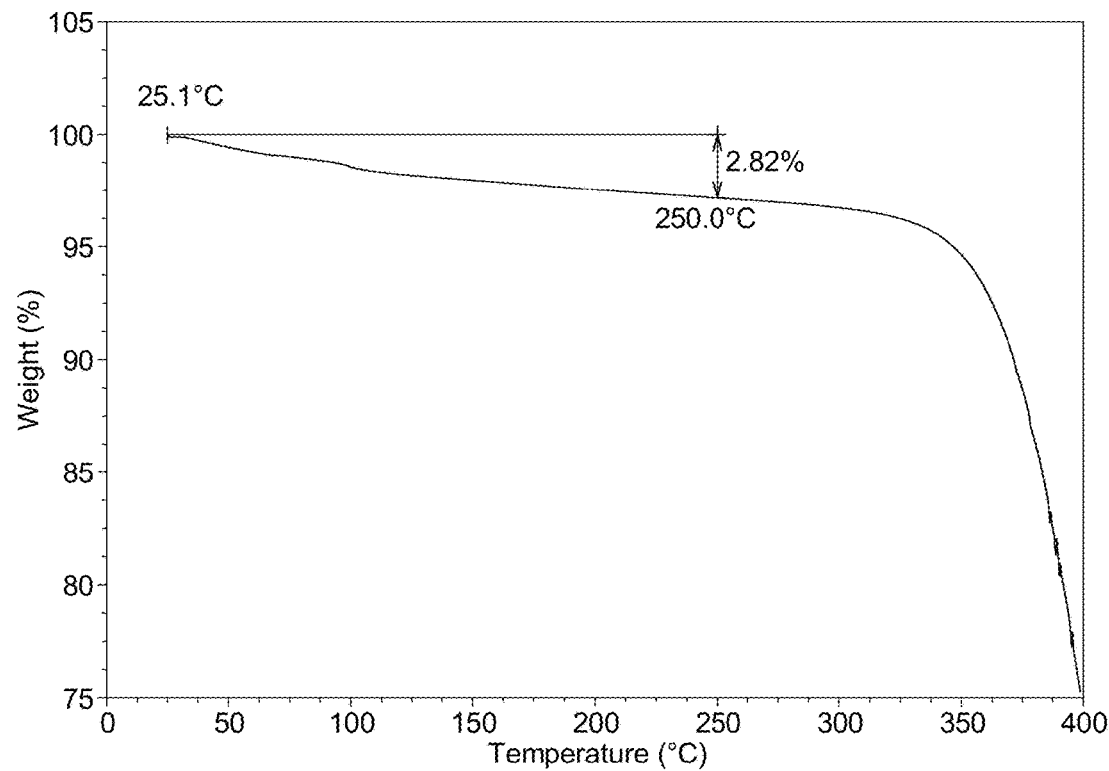
FIG. 3 shows a TGA curve of Type A in a hydrate form.

The hydrated Type A shows 2.8% weight loss when heated to 250° C., and the TGA curve is depicted in FIG. 3.

The anhydrous Type A shows 2.2% weight loss when heated to 200° C. in the TGA curve.

Type A of present disclosure shows a solubility of 0.013 mg/mL after equilibrium in water at room temperature for 24 hours.

Type B Crystalline Form

Type B crystalline form can be prepared from Type A by different crystallization methods, e.g., anti-solvent addition and slow cooling and slurry.

Figure 4:
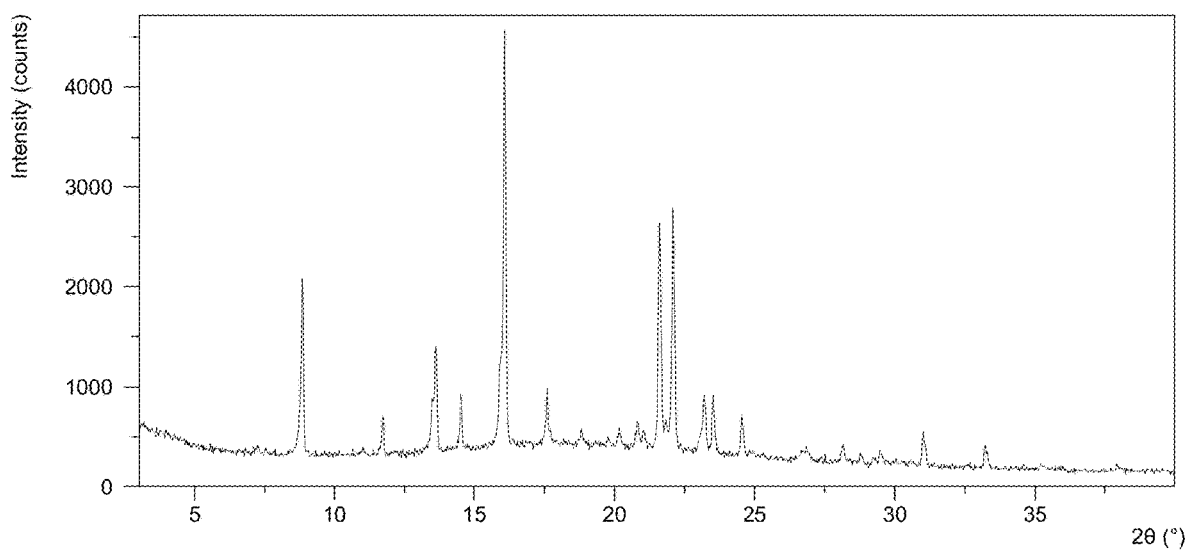
FIG. 4 shows an XRPD pattern of Type B.

The XRPD of Type B of present invention is shown in FIG. 4, which shows the most intense peaks at 2theta values of 16.1°±0.2°, 22.1°±0.2°, 21.6°±0.2°.

Furthermore, the XRPD of Type B further shows one or more characteristic peaks at 2theta values of 8.8°±0.2°, 13.6°±0.2°, 23.2°±0.2°.

Furthermore, the XRPD of Type B further shows one or more characteristic peaks at 2theta values of 17.6°±0.2°, 14.5°±0.2°, 24.5°±0.2°.

The XRPD data of Type B is shown in Table 2.

TABLE 2

| 2theta | d spacing | Intensity (%) |
|---|---|---|
| 8.83 | 10.01 | 45.83 |
| 13.57 | 6.53 | 36.35 |
| 14.51 | 6.10 | 20.80 |
| 15.03 | 5.89 | 10.88 |
| 16.06 | 5.52 | 100.00 |
| 17.69 | 5.01 | 6.28 |
| 20.99 | 4.23 | 20.08 |
| 21.58 | 4.12 | 47.22 |
| 22.06 | 4.03 | 72.29 |
| 23.17 | 3.84 | 26.40 |
| 23.51 | 3.78 | 8.45 |
| 24.50 | 3.63 | 9.17 |
| 26.75 | 3.33 | 5.00 |
| 28.16 | 3.17 | 8.63 |
| 31.00 | 2.88 | 8.41 |
| 33.20 | 2.70 | 8.08 |

Type B is an anhydrate.

Figure 5:
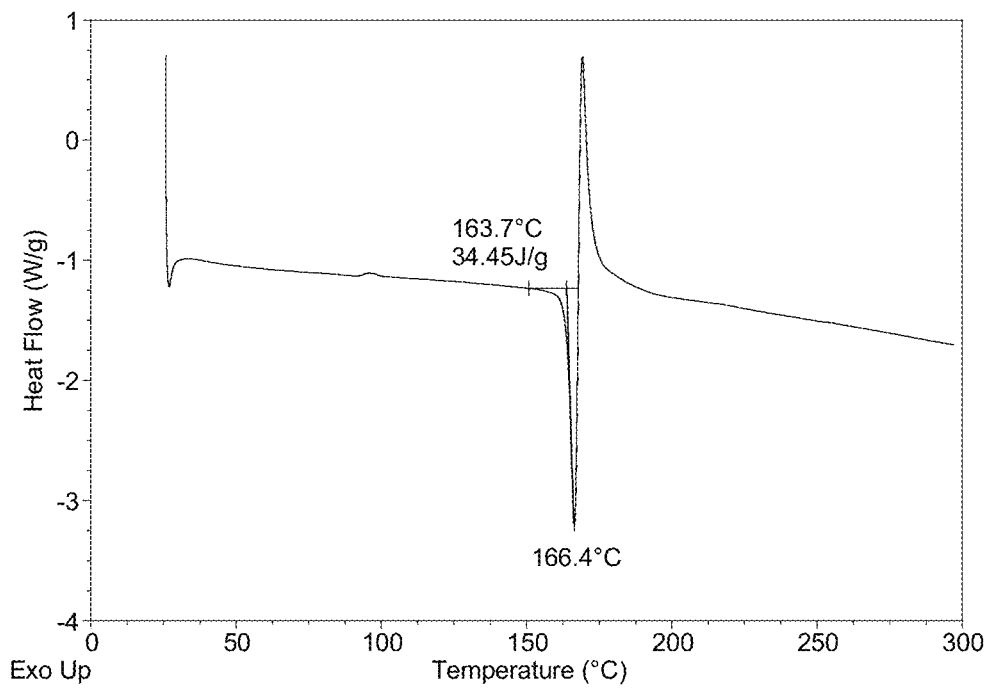
FIG. 5 shows a DSC curve of Type B.

Type B shows an endothermic peak when heated to around 164° C. (onset temperature), and the DSC curve is depicted in FIG. 5.

Figure 6:
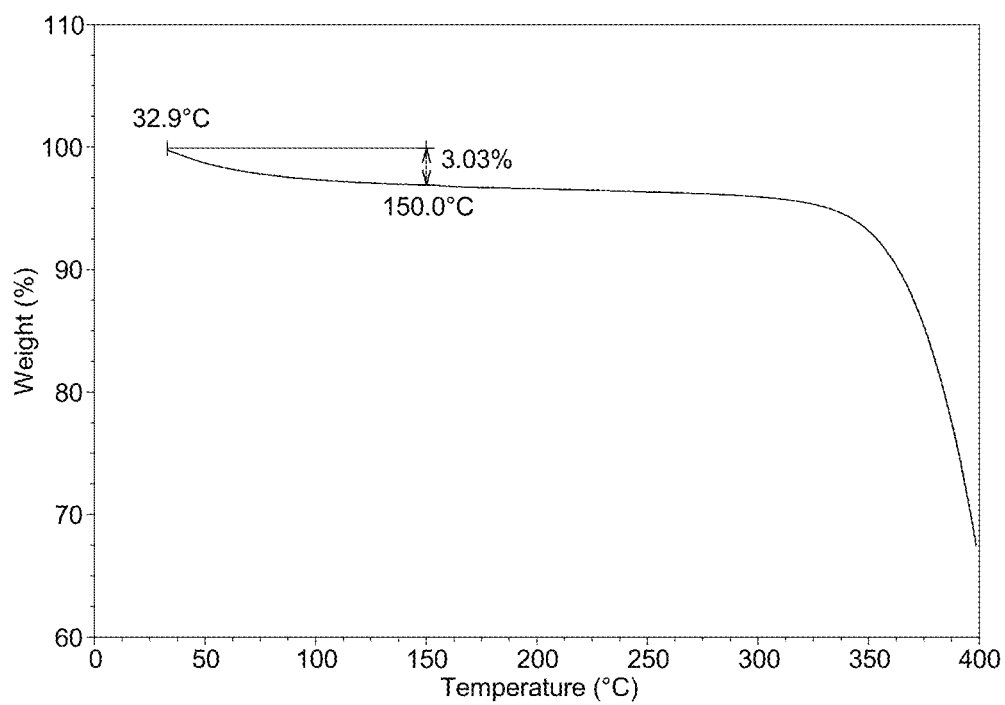
FIG. 6 shows a TGA curve of Type B.

Type B of present disclosure shows 3.0% weight loss when heated to 150° C., and the TGA curve is depicted in FIG. 6.

Type B shows a solubility of 0.006 mg/mL after equilibrium in water at room temperature for 24 hours.

Type C Crystalline Form

Type C crystalline form can be prepared from Type A by different crystallization methods such as slow evaporation, slow cooling, slurry, and liquid vapor diffusion in different solvent systems.

Figure 7:
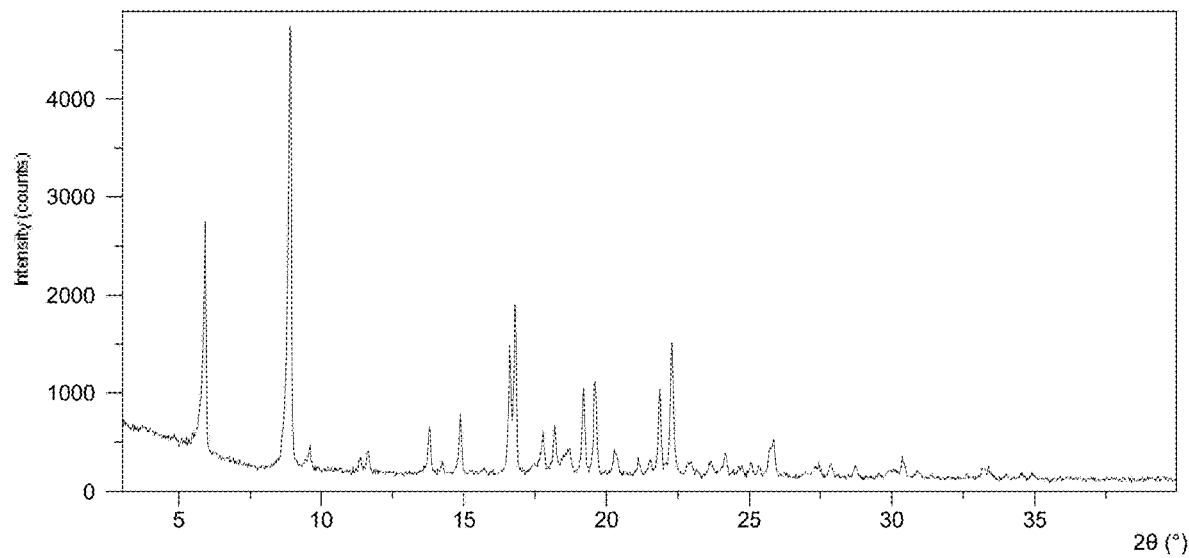
FIG. 7 shows an XRPD pattern of Type C.

The XRPD of Type C of present invention is shown in FIG. 7, which shows the most intense peaks at 2theta values of 8.4°±0.2°, 5.4°±0.2°, 16.3°±0.2°.

Furthermore, the XRPD of Type C further shows one or more characteristic peaks at 2theta values of 16.1°±0.2°, 18.7°±0.2°, 21.8°±0.2°.

Furthermore, the XRPD of Type C further shows one or more characteristic peaks at 2theta values of 21.3°±0.2°, 17.6°±0.2°, 14.3°±0.2°.

The XRPD data of Type C is shown in Table 3.

TABLE 3

| 2theta | d spacing | Intensity (%) |
|---|---|---|
| 5.40 | 16.37 | 57.16 |
| 8.37 | 10.56 | 100.00 |
| 9.04 | 9.79 | 4.48 |
| 11.08 | 7.98 | 5.22 |
| 13.26 | 6.68 | 11.05 |
| 13.67 | 6.48 | 2.01 |
| 14.32 | 6.18 | 11.76 |
| 16.08 | 5.51 | 26.99 |
| 16.27 | 5.45 | 30.98 |
| 17.26 | 5.14 | 9.00 |
| 17.66 | 5.02 | 12.67 |

TABLE 3-continued

| 2theta | d spacing | Intensity (%) |
|---|---|---|
| 18.10 | 4.90 | 7.36 |
| 18.65 | 4.76 | 24.56 |
| 19.08 | 4.65 | 22.51 |
| 19.83 | 4.48 | 4.25 |
| 20.58 | 4.32 | 3.32 |
| 20.95 | 4.24 | 4.56 |
| 21.34 | 4.16 | 14.04 |
| 21.75 | 4.09 | 22.38 |
| 22.35 | 3.98 | 3.19 |
| 23.08 | 3.85 | 2.37 |
| 23.62 | 3.77 | 5.59 |
| 24.15 | 3.69 | 1.98 |
| 24.54 | 3.63 | 2.37 |
| 24.81 | 3.59 | 2.46 |
| 25.20 | 3.53 | 5.64 |
| 26.87 | 3.32 | 2.24 |
| 27.35 | 3.26 | 2.70 |
| 29.89 | 2.99 | 2.50 |
| 32.74 | 2.74 | 1.23 |

Type C is an isomorphic form, i.e. having cavities/voids in the crystal structure to allow participation of various guest molecules with appropriate size.

Figure 8:
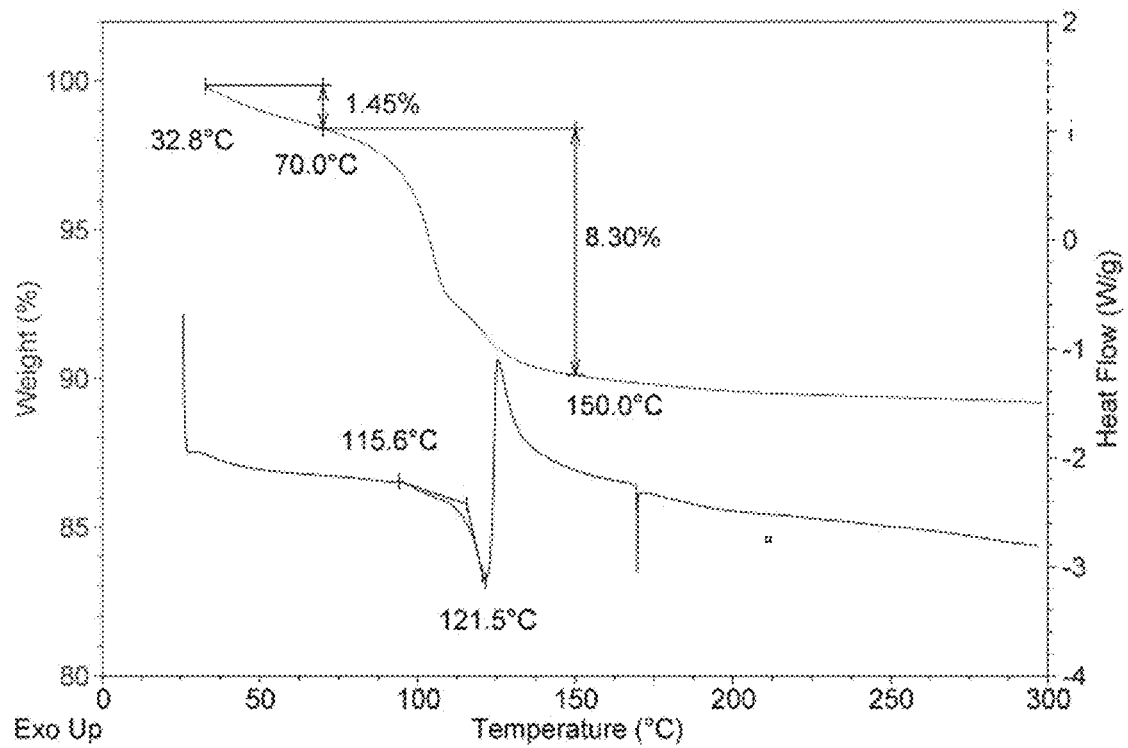
FIG. 8 shows an DSC and TGA curves of Type C.

Type C shows an endothermic peak when heated to around 116° C. (onset temperature). Type C shows a step weight loss of 8.3% between 70° C. and 150° C. The DSC and TGA curves are depicted in FIG. 8.

Type C and A possess similar XRPD patterns except the discrepancies at 15-20° region. Type C and A are potentially in the same crystal family, i.e. with similar lattice structure.

Type D Crystalline Form

Type D crystalline form can be prepared from Type A by slow evaporation from methanol at room temperature.

Figure 9:
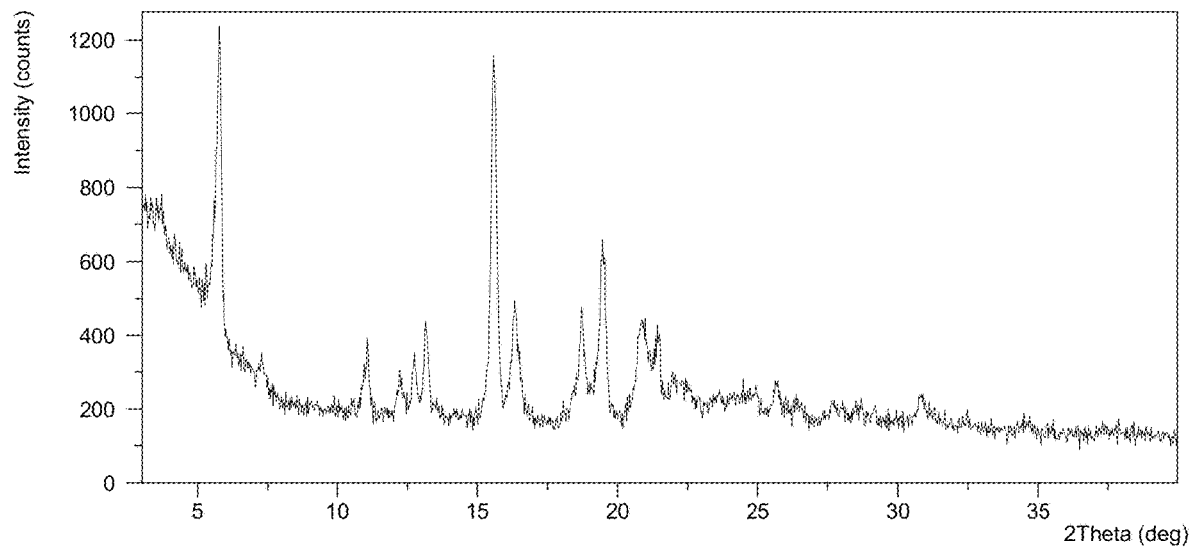
FIG. 9 shows an XRPD pattern of Type D.

The XRPD of Type D of the present invention is shown in FIG. 9, which shows the most intense peaks at 2theta values of 5.2°±0.2°, 15.0°±0.2°, 18.9°±0.2°.

Furthermore, the XRPD of Type D further shows one or more characteristic peaks at 2theta values of 19.0°±0.2°, 20.4°±0.2°, 12.6°±0.2°.

Furthermore, the XRPD of Type D further shows one or more characteristic peaks at 2theta values of 20.9°±0.2°, 15.7°±0.2°, 12.2°±0.2°.

The XRPD data of Type D is shown in Table 4.

TABLE 4

| 2theta | d spacing | Intensity (%) |
|---|---|---|
| 2.96 | 29.80 | 52.55 |
| 5.25 | 16.84 | 100.00 |
| 6.78 | 13.04 | 11.85 |
| 10.52 | 8.41 | 19.75 |
| 11.67 | 7.58 | 9.85 |
| 12.19 | 7.26 | 14.47 |
| 12.61 | 7.02 | 24.19 |
| 15.02 | 5.90 | 94.65 |
| 15.81 | 5.61 | 31.14 |
| 18.18 | 4.88 | 30.09 |
| 18.89 | 4.70 | 42.66 |
| 20.27 | 4.38 | 22.09 |
| 20.90 | 4.25 | 18.75 |
| 25.16 | 3.54 | 7.42 |
| 30.31 | 2.95 | 6.91 |

Type D of present disclosure is a hydrate.

Figure 10:
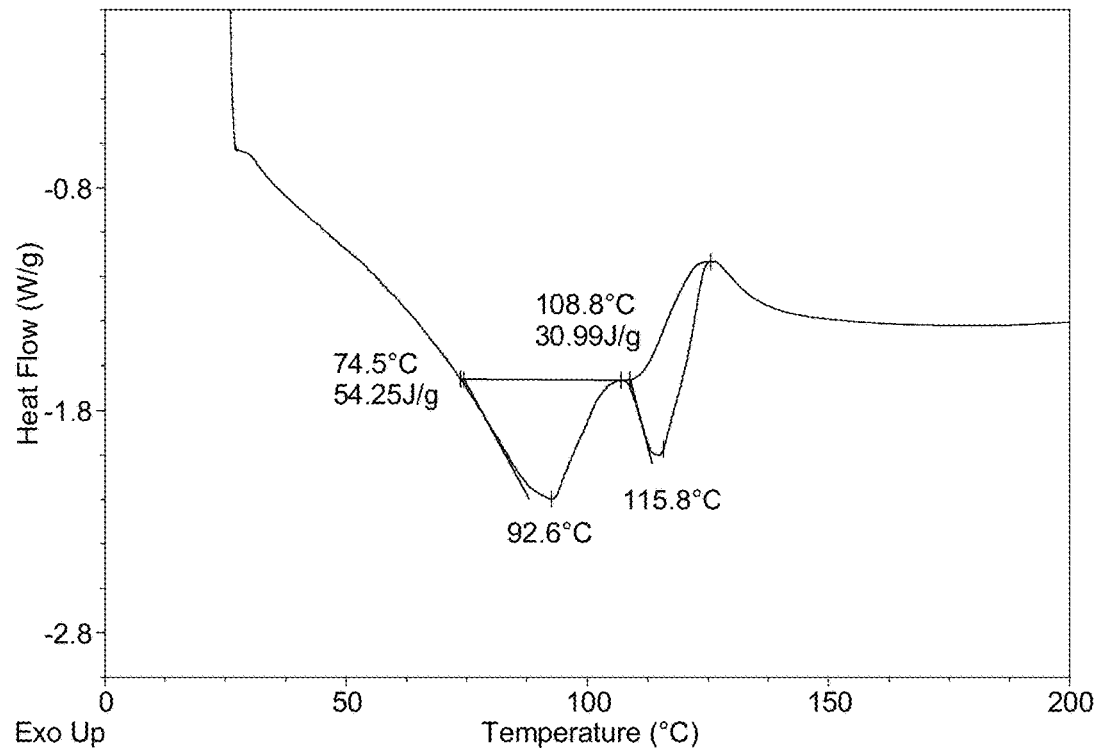
FIG. 10 shows a DSC curve of Type D.

Type D of present disclosure shows two endothermic peaks when heated to around 75° C. (onset temperature) and 109° C. (onset temperature), and the DSC curve is depicted in FIG. 10.

Figure 11:
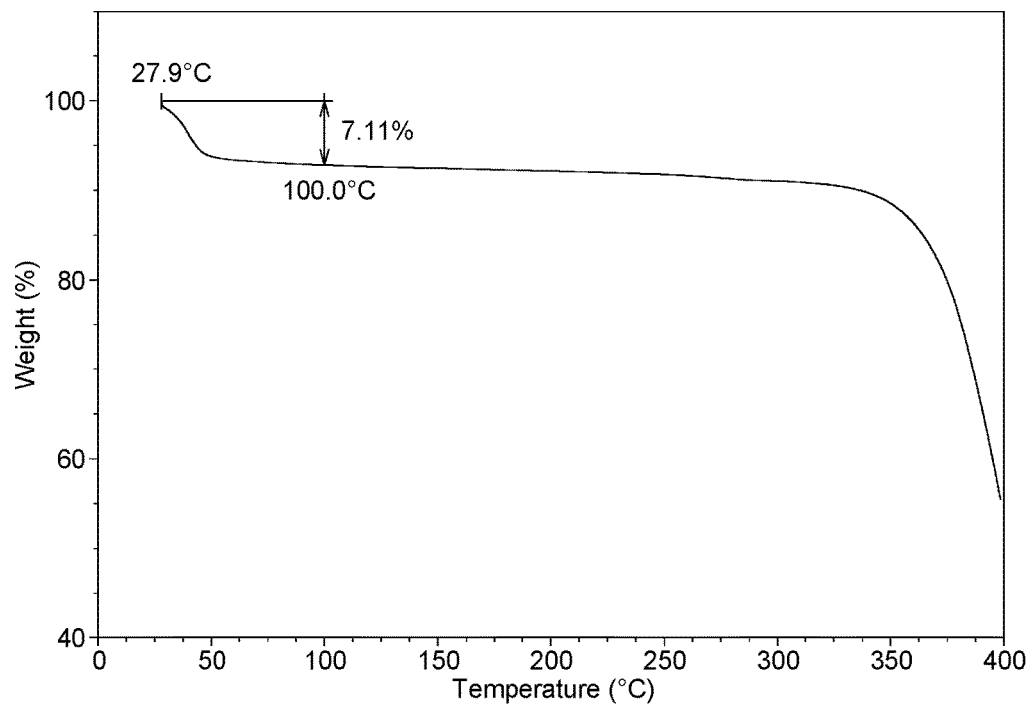
FIG. 11 shows a TGA curve of Type D.

Type D of present disclosure shows 7.1% weight loss when heated to 100° C., and the TGA curve is depicted in FIG. 11.

Type D of present disclosure shows a solubility of 0.018 mg/mL after equilibrium in water at room temperature for 24 hours.

Type E Crystalline Form

Figure 12:
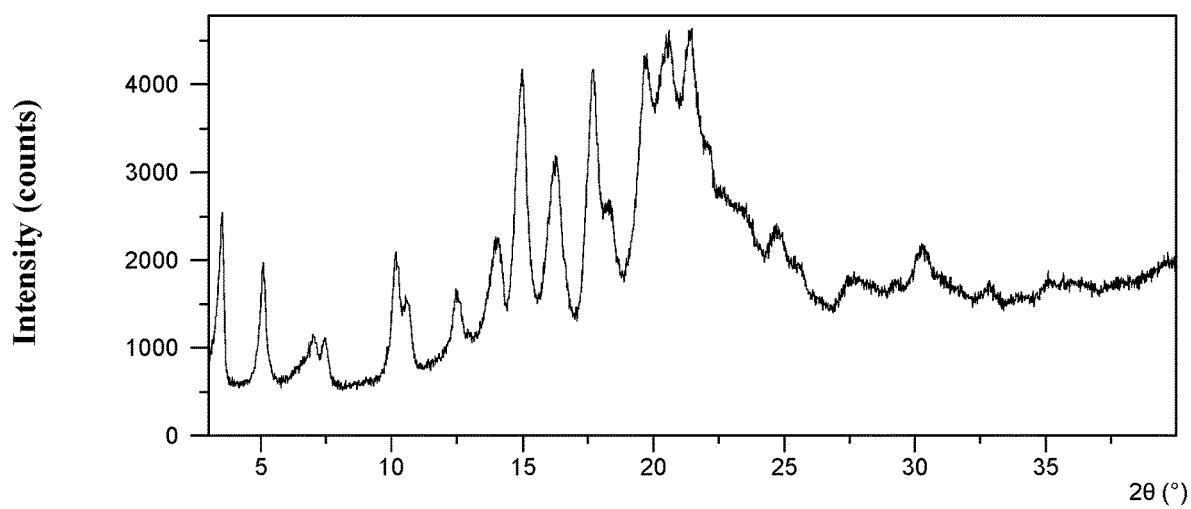
FIG. 12 shows an XRPD pattern of Type E.

Type E can be prepared by purging Type D under $N_2$ or heating Type D to over 100° C. The XRPD of Type E of present invention is shown in FIG. 12, which shows characteristic peaks at 2theta values of 21.4°±0.2°, 20.7°±0.2°, 19.7°±0.2°.

Furthermore, the XRPD of Type E further shows one or more characteristic peaks at 2theta values of 17.7°±0.2°, 15.0°±0.2°, 16.3°±0.2°.

Furthermore, the XRPD of Type E further shows one or more characteristic peaks at 2theta values of 3.5°±0.2°, 10.1°±0.2°, 14.1°±0.2°.

The XRPD data of Type E is shown in Table 5.

TABLE 5

| 2theta | d spacing | Intensity (%) |
|---|---|---|
| 3.51 | 25.18 | 54.63 |
| 5.06 | 17.45 | 37.86 |
| 7.00 | 12.63 | 15.73 |
| 7.47 | 11.83 | 14.79 |
| 10.15 | 8.72 | 40.13 |
| 10.68 | 8.29 | 22.10 |
| 12.44 | 7.12 | 24.11 |
| 14.10 | 6.28 | 39.63 |
| 15.03 | 5.89 | 89.81 |
| 16.13 | 5.50 | 58.50 |
| 16.27 | 5.45 | 64.29 |
| 17.69 | 5.01 | 91.92 |
| 18.41 | 4.82 | 45.67 |
| 19.69 | 4.51 | 93.87 |
| 20.66 | 4.30 | 96.16 |
| 21.42 | 4.15 | 100.00 |
| 22.18 | 4.00 | 61.56 |
| 23.67 | 3.76 | 36.26 |
| 24.89 | 3.58 | 30.86 |
| 25.65 | 3.47 | 19.45 |
| 27.50 | 3.24 | 13.61 |
| 30.19 | 2.96 | 19.71 |
| 32.86 | 2.73 | 5.63 |

Type E is an anhydrate.

Type F Crystalline Form

Type F can be prepared from Type A, B, or D, via slurry in a solvent or a solvent mixture (e.g., methanol, ethanol, acetonitrile, methanol/water, or ethanol/water).

Figure 13:
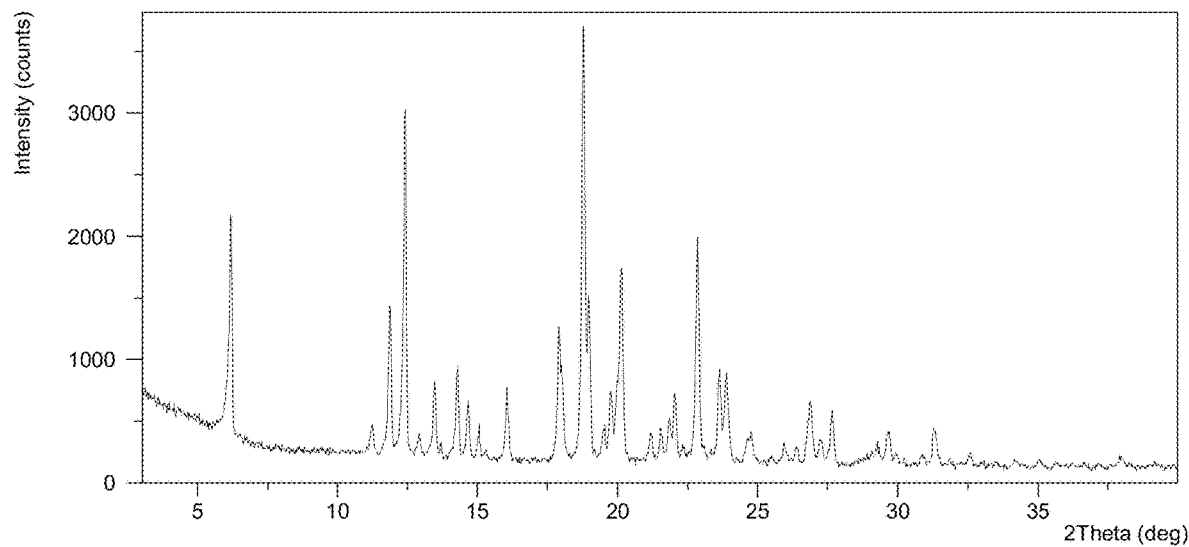
FIG. 13 shows an XRPD pattern of Type F.

The XRPD of Type F of present invention is shown in FIG. 13, which shows the most intense peaks at 2theta values of 18.7°±0.2°, 12.4°±0.2°, 22.8°±0.2°.

Furthermore, the XRPD of Type F further shows one or more characteristic peaks at 2theta values of 17.9°±0.2°, 20.1°±0.2°, 11.8°±0.2°.

Furthermore, the XRPD of Type F further shows one or more characteristic peaks at 2theta values of 23.8°±0.2°, 14.2°±0.2°, 6.2°±0.2°.

The XRPD data of Type F is shown in Table 6.

TABLE 6

| 2theta | d spacing | Intensity (%) |
|---|---|---|
| 6.18 | 14.30 | 47.96 |
| 11.20 | 7.90 | 6.61 |
| 11.85 | 7.47 | 33.51 |
| 12.38 | 7.15 | 77.36 |
| 12.88 | 6.87 | 3.98 |
| 13.43 | 6.59 | 16.62 |
| 14.25 | 6.22 | 20.00 |
| 14.64 | 6.05 | 11.77 |
| 15.03 | 5.89 | 6.50 |
| 16.05 | 5.52 | 15.91 |
| 17.89 | 4.96 | 30.09 |
| 18.75 | 4.73 | 100.00 |
| 18.96 | 4.68 | 35.16 |
| 19.48 | 4.56 | 7.84 |
| 19.75 | 4.50 | 15.42 |
| 20.12 | 4.41 | 43.61 |
| 21.16 | 4.20 | 6.47 |
| 21.52 | 4.13 | 7.51 |
| 21.81 | 4.07 | 9.82 |
| 22.03 | 4.04 | 15.23 |
| 22.81 | 3.90 | 47.92 |
| 23.61 | 3.77 | 20.50 |
| 23.86 | 3.73 | 20.57 |
| 24.74 | 3.60 | 6.37 |
| 25.94 | 3.43 | 4.67 |
| 26.38 | 3.38 | 3.62 |
| 26.87 | 3.32 | 13.70 |
| 27.22 | 3.28 | 5.36 |
| 27.65 | 3.23 | 11.63 |
| 29.22 | 3.06 | 4.23 |
| 29.66 | 3.01 | 6.86 |
| 31.28 | 2.86 | 8.51 |
| 32.54 | 2.75 | 2.45 |
| 34.24 | 2.62 | 0.99 |
| 35.03 | 2.56 | 1.43 |
| 37.95 | 2.37 | 2.10 |

Type F is an anhydrate.

Figure 14:
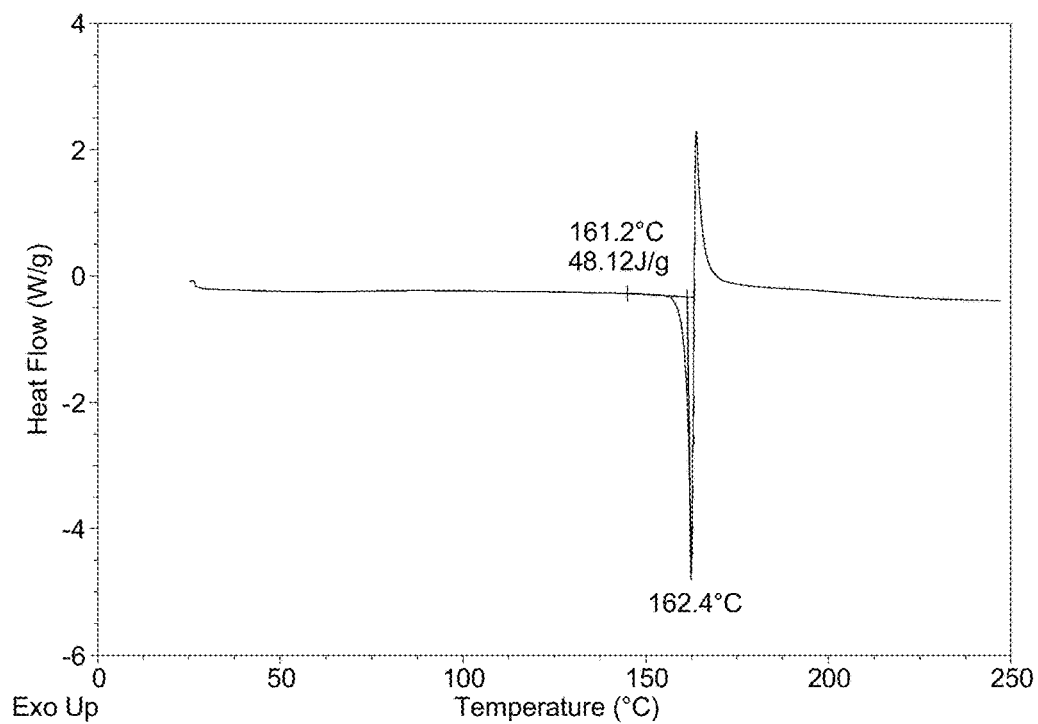
FIG. 14 shows a DSC curve of Type F.

Type F of present disclosure shows an endothermic peak when heated to around 161° C. (onset temperature), and the DSC curve is depicted in FIG. 14.

Figure 15:
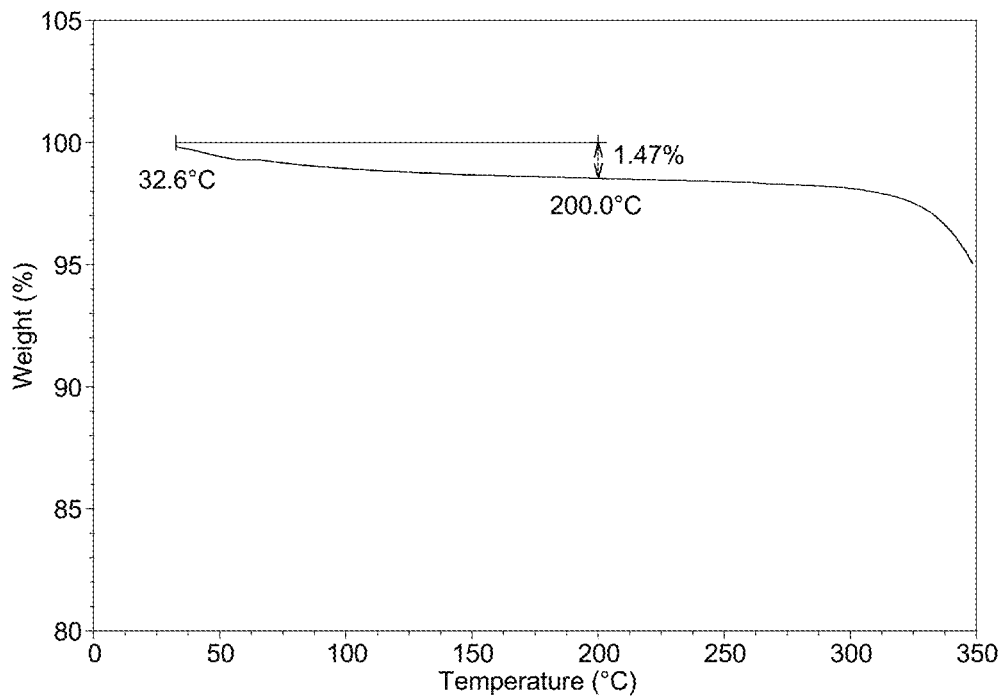
FIG. 15 shows a TGA curve of Type F.

Type F of present disclosure shows 1.5% weight loss when heated to 200° C., and the TGA curve is depicted in FIG. 15.

Type F of present disclosure shows a solubility of 0.004 mg/mL after equilibrium in water at room temperature for 24 hours.

Pharmaceutical Composition

The present invention is also directed to a pharmaceutical composition comprising a therapeutically effective amount of Type A, Type B, Type C, Type D, or Type F, or a mixture thereof, in any ratio, and a pharmaceutically acceptable carrier.

The crystalline forms of Type A, Type B, Type D, and Type F are useful as an active pharmaceutical ingredient (API) in a pharmaceutical composition, with Type F being preferred.

Pharmaceutically acceptable carriers, which are inactive ingredients, can be selected by those skilled in the art using conventional criteria. Pharmaceutically acceptable carriers include, but are not limited to, non-aqueous based solutions, suspensions, emulsions, microemulsions, micellar solutions, gels, and ointments. The pharmaceutically acceptable carriers may also contain ingredients that include, but are not limited to, saline and aqueous electrolyte solutions; ionic and nonionic osmotic agents such as sodium chloride, potassium chloride, glycerol, and dextrose; pH adjusters and buffers such as salts of hydroxide, phosphate, citrate, acetate, borate, and trolamine; antioxidants such as salts, acids and/or bases of bisulfite, sulfite, metabisulfite, thiosulfite, ascorbic acid, acetyl cysteine, cystein, glutathione, butylated hydroxyanisole, butylated hydroxytoluene, tocopherols, and ascorbyl palmitate; surfactants such as lecithin, phospholipids, including but not limited to phosphatidylcholine, phosphatidylethanolamine and phosphatidyl inositiol; poloxamers and ploxamines, polysorbates such as polysorbate 80, polysorbate 60, and polysorbate 20, polyethers such as polyethylene glycols and polypropylene glycols; polyvinyls such as polyvinyl alcohol and povidone; cellulose derivatives such as methylcellulose, hydroxypropyl cellulose, hydroxyethyl cellulose, carboxymethyl cellulose and hydroxypropyl methylcellulose and their salts; petroleum derivatives such as mineral oil and white petrolatum; fats such as lanolin, peanut oil, palm oil, soybean oil; mono-, di-, and triglycerides; polymers of acrylic acid such as carboxypolymethylene gel, and hydrophobically modified cross-linked acrylate copolymer; polysaccharides such as dextrans and glycosaminoglycans such as sodium hyaluronate. Such pharmaceutically acceptable carriers may be preserved against bacterial contamination using well-known preservatives, these include, but are not limited to, benzalkonium chloride, ethylene diamine tetra-acetic acid and its salts, benzethonium chloride, chlorhexidine, chlorobutanol, methylparaben, thimerosal, and phenylethyl alcohol, or may be formulated as a non-preserved formulation for either single or multiple use.

For example, a tablet formulation or a capsule formulation of Type A, B, C, D, or F form of Compound I may contain other excipients that have no bioactivity and no reaction with the active compound. Excipients of a tablet may include fillers, binders, lubricants and glidants, disintegrators, wetting agents, and release rate modifiers. Binders promote the adhesion of particles of the formulation and are important for a tablet formulation. Examples of binders include, but not limited to, carboxymethylcellulose, cellulose, ethylcellulose, hydroxypropylmethylcellulose, methylcellulose, karaya gum, starch, starch, and tragacanth gum, poly(acrylic acid), and polyvinylpyrrolidone.

For example, a patch formulation of Type A, B, C, D, or F form of Compound I may comprise some inactive ingredients such as 1,3-butylene glycol, dihydroxyaluminum aminoacetate, disodium edetate, D-sorbitol, gelatin, kaolin, methylparaben, polysorbate 80, povidone, propylene glycol, propylparaben, sodium carboxymethylcellulose, sodium polyacrylate, tartaric acid, titanium dioxide, and purified water. A patch formulation may also contain skin permeability enhancer such as lactate esters (e.g., lauryl lactate) or diethylene glycol monoethylether.

The crystalline forms of Type A, Type B, Type D, and Type F show at least one advantage in stability, solubility and hygroscopicity, and they are suitable for pharmaceutical research and manufacturing.

Type A is stable after storage at 80° C. (closed) for 1 day and 25° C./60% RH, 40° C./75% RH (open) for 1 week.

Type B is stable after storage at 80° C. (closed) for 1 day and 25° C./60% RH, 40° C./75% RH (open) for 1 week. Type B shows a water uptake of 0.5% at 80% RH and is slightly hygroscopic, and Type B shows no form change after DVS test.

Type D is stable after storage at 25° C./60% RH, 40° C./75% RH (open) for 1 week. Type F is stable after storage at 80° C. (closed) for 1 day and 25° C./60% RH, 40° C./75% RH (open) for 1 week. Type F shows a water uptake of 1.2% at 80% RH and is slightly hygroscopic, and Type F shows no form change after DVS test.

Slurry competition experiments confirmed that Type A, B and D converted into anhydrate Type F after slurry in various solvent systems. Type A and F showed relatively good physical and chemical stability under 25° C./60% RH and 40° C./75% RH conditions for one week except that Type D converted to the mixture of Type B and D under 80° C. for 1 day. The equilibrium solubility of Type A, B, D and F in $H_2O$ is 0.013, 0.006, 0.018 and 0.004 mg/mL. DVS confirmed that Type B and F are slightly hygroscopic, Type A is hygroscopic and Type D is a relative stable hydrate. Crystallinity of Type A was decreased after stored at 92.5% RH for about 17 days.

Type F is the thermodynamically more stable form than Type A/B/D between RT to 50/70° C.

The following examples further illustrate the present invention. These examples are intended merely to be illustrative of the present invention and are not to be construed as being limiting.

EXAMPLES

XRPD studies was performed using a Panalytical Empyrean X-ray powder diffractometer. The parameters of the X-ray powder diffraction of the present disclosure are as follows:

X-ray Reflection: Cu, Kα
  Kα1 (Å): 1.540598; Kα2 (Å): 1.544426
  Kα2/Kα1 intensity ratio: 0.50
Voltage: 45 (kV)
Current: 40 (mA)
Scanning range: from 3.0 degree to 40.0 degree
DSC data in the present disclosure were acquired by a TA Q2000. The parameters of the DSC method of the present disclosure were as follows:
Heating rate: 10° C./min
Purge gas: nitrogen
TGA data in the present disclosure are acquired by a TA Q5000. The parameters of the TGA method of the present disclosure were as follow:
Heating rate: 10° C./min
Purge gas: nitrogen
Dynamic vapor sorption (DVS) data in the present disclosure were acquired by a SMS (Surface Measurement Systems) DVS Intrinsic. The parameters of the dynamic vapor sorption (DVS) method of the present disclosure were as follows:
Temperature: 25° C.
Gas and flow rate: nitrogen, 200 mL/min
dm/dt: 0.002%/min
RH range: 0% RH-95% RH Example 1. Preparation of Type A The starting material Compound I was prepared according to the procedures described in Example 3 of WO2015/048662. The starting material Compound I was dissolved in dichloromethane; ethyl acetate was then added dropwise with stirring until solid was precipitated out. The solid was isolated by filtration and washed with ethyl acetate.

The XRPD data of Type A comprise diffraction peaks listed in Table 1. The XRPD pattern is displayed in FIG. 1. The DSC curve is displayed in FIG. 2. The TGA curve is displayed in FIG. 3.

Example 2. Preparation of Type B

Type B can be prepared by the following different methods. The XRPD data of different preparations are all similar (containing the same major diffraction peaks).

15.1 mg of Type A was dissolved in 0.4 mL of N-methyl pyrrolidone and 4 mL of $H_2O$ was then added dropwise with stirring to give a suspension. Type B was obtained by centrifugation, followed by drying. The XRPD data of Type B prepared by this method comprise diffraction peaks as shown in Table 2. The XRDP pattern is displayed in FIG. 4. The DSC curve is displayed in FIG. 5. The TGA curve is displayed in FIG. 6.

15.1 mg of Type A was dissolved in 1.4 mL of acetonitrile and 8 mL of $H_2O$ was then added dropwise with stirring to give a suspension. Type B was obtained by centrifugation, followed by drying.

25.2 mg of Type A was added into 2.0 mL of acetonitrile/$H_2O$ (1:1, v/v) and the resulting mixture was stirred at 50° C. for 2 hours. After filtration, the filtrate was slowly cooled down to 5° C. at 0.1° C./min to give a suspension. Type B was obtained by centrifugation, following by drying.

15.0 mg of Type A was added into 0.5 mL of acetonitrile and the resulting mixture was stirred at room temperature for 72 hours. Type B was obtained by centrifugation, following by drying.

15.0 mg of Type A was added into 0.5 mL of acetonitrile/$H_2O$ (1:1, v/v) and the resulting mixture was stirred at room temperature for 72 hours. Type B was obtained by centrifugation, followed by drying.

15.6 mg of Type A was added into 0.5 mL of N,N-dimethylformamide, then the mixture was stirred at room temperature for 72 hours. Type B was obtained by centrifugation and drying.

79.7 mg of Type A was added into 3.5 mL of ethanol and then filtered. To the filtrate was added 1 mg of Type B seeds, followed by addition of 14 mL of $H_2O$ dropwise at room temperature to give a suspension. Type B was obtained by centrifugation, followed by drying.

Example 3. Preparation of Type C 14.9 mg of Type A was added into 0.3 mL of methyl isobutyl ketone and the resulting mixture was stirred at 50° C. for 72 hours. Type C was obtained by centrifugation, following by drying.

Example 4. Preparation of Type D 14.4 mg of Type A was dissolved in 0.6 mL of methanol, the solution was filtered and evaporated at room temperature to obtain Type D. The XRPD data of Type D prepared in this example comprise diffraction peaks listed in Table 4. The XRPD pattern is displayed in FIG. 9.

Example 5. Preparation of Type E

Type E was only observed in-situ after either purging hydrate Type D sample under $N_2$ at 30° C. for 30 minutes or heating to 105° C. The XRPD pattern of Type E is displayed in FIG. 12.

Example 6. Preparation of Type F

Type F can be prepared by the following different methods. The XRPD data of different preparations are all similar (containing the same major diffraction peaks).

100.1 mg of Type A was added into 2.5 mL of acetonitrile, and the resulting mixture was stirred at room temperature for 20 days. Type F was obtained after centrifugation and drying.

100 mg of Type A was added into 15 mL of water. After addition of 1 mg of Type F seeds, the mixture was stirred at 50° C. for 2 hours. Type F was obtained after vacuum filtration and drying.

20.9 mg of Type A was added into 2 mL of n-propanol. After stirring at 50° C. for 1 hour, the mixture was filtered and to the filtrate was added 1 mg of Type F seeds, followed by 12 mL of $H_2O$ dropwise at 50° C. with stirring. Type F was obtained by centrifugation and drying. The XRPD data of Type F prepared by this method comprise diffraction peaks listed in Table 6. The XRPD pattern is displayed in FIG. 13.

Example 7. Stability Assessment of Type A

Approximate 10 mg of Type A sample was added into each 1.5-mL glass vial and stored at 80° C. (closed) for 1 day, 25° C./60% RH and 40° C./75% RH (open) for 1 week, then tested by XRPD and HPLC purity. The assessment results are shown in Table 7.

The XRPD patterns of Type A before and after storage at 80° C. for 1 day, the XRPD patterns of Type A before and after storage at 25° C./60% RH for 1 week, and the XRPD patterns of Type A before and after storage at 40° C./75% RH for 1 week all show little or no change.

The results show that Type A did not change at 80° C. (closed) for 1 day, 25° C./60% RH, and 40° C./75% RH (open) for 1 week, and there was no decrease in purity.

TABLE 7

| | Initial | 80° C./1 day | | 25° C./60% RH/1 week | | 40° C./75% RH/1 week | |
|---|---|---|---|---|---|---|---|
| Initial form | purity (area %) | Purity/initial purity (%) | Final form | Purity/initial purity (%) | Final form | Purity/initial purity (%) | Final form |
| A | 99.5 | 100.0 | A | 100.0 | A | 100.1 | A |

Example 8. Stability Assessment of Type B

Approximate 4 mg of Type B sample was added into each 1.5-mL glass vial and stored at 80° C. (closed) for 1 day, 25° C./60% RH and 40° C./75% RH (open) for 1 week, then tested by XRPD and HPLC purity. The assessment results are shown in Table 8.

The XRPD patterns of Type B before and after storage at 80° C. for 1 day, the XRPD patterns of Type B before and after storage at 25° C./60% RH for 1 week, and the XRPD patterns of Type B before and after storage at 40° C./75% RH for 1 week all show little or no change.

The results show that Type B did not change at 80° C. (closed) for 1 day, 25° C./60% RH, and 40° C./75% RH (open) for 1 week, and there was no decrease in purity.

TABLE 8

| Initial form | Initial purity (area %) | 80° C./1 day | | 25° C./60% RH/1 week | | 40° C./75% RH/1 week | |
|---|---|---|---|---|---|---|---|
| | | Purity/initial purity (%) | Final form | Purity/initial purity (%) | Final form | Purity/initial purity (%) | Final form |
| B | 99.9 | 99.7 | B | 99.5 | B | 99.7 | B |

Example 9. Hygroscopicity Assessment of Type B

Approximate 10 mg of Type B sample in the present disclosure was assessed by hygroscopicity using a dynamic vapor sorption (DVS) instrument, and tested by XRPD before and after DVS test. The results show that Type B had a water uptake of 0.5% under 80% RH, indicating that Type B is slightly hygroscopic. The XRPD patterns of Type B did not change before and after DVS test.

The definition of hygroscopicity refers to Chinese Pharmacopeia 2010 (testing condition: 25° C.±1° C., 80% relative humidity):

Deliquescent: sufficient water is absorbed to form a liquid

Very hygroscopic: increase in mass is equal to or greater than 15%

Hygroscopic: increase in mass is less than 15% and equal to or greater than 2%

Slightly hygroscopic: increase in mass is less than 2% and equal to or greater than 0.2%

Non-hygroscopic: increase in mass is less than 0.2%

Example 10. Stability Assessment of Type D

Approximate 4 mg of Type D sample was added into each 1.5-mL glass vial and stored at 25° C./60% RH and 40° C./75% RH (open) for 1 week, then tested by XRPD and HPLC purity. The assessment results are shown in Table 9.

The XRPD patterns of Type D before and after storage at 25° C./60% RH for 1 week, and the XRPD patterns of Type D before and after storage at 40° C./75% RH for 1 week all show little or no change. However, the XRPD patterns of Type D before and after storage at 80° C. for 1 day shows Type D converted to a mixture of Type B and D.

The results show that Type D did not change at 25° C./60% RH and 40° C./75% RH (open) for 1 week, and there was no significant decrease in purity.

TABLE 9

| Initial form | Initial purity (area %) | 25° C./60% RH/1 week | | 40° C./75% RH/1 week | |
|---|---|---|---|---|---|
| | | Purity/initial purity (%) | Final form | Purity/initial purity (%) | Final form |
| D | 99.7 | 99.9 | D | 99.9 | D |

Example 11. Stability Assessment of Type F

Approximate 7 mg of Type F sample was added into each 1.5-mL glass vial and stored at 80° C. (closed) for 1 day, 25° C./60% RH and 40° C./75% RH (open) for 1 week, then tested by XRPD and HPLC purity. The assessment results are shown in Table 10.

The XRPD patterns of Type F before and after storage at 80° C. for 1 day, the XRPD patterns of Type F before and after storage at 25° C./60% RH for 1 week, and the XRPD patterns of Type F before and after storage at 40° C./75% RH for 1 week all show little or no change.

The results show that Type F did not change at 80° C. (closed) for 1 day, 25° C./60% RH, and 40° C./75% RH (open) for 1 week, and there was no decrease in purity.

TABLE 10

| Initial form | Initial purity (area %) | 80° C./1 day | | 25° C./60% RH/1 week | | 40° C./75% RH/1 week | |
|---|---|---|---|---|---|---|---|
| | | Purity/initial purity (%) | Final form | Purity/initial purity (%) | Final form | Purity/initial purity (%) | Final form |
| F | 100.0 | 100.0 | F | 100.0 | F | 100.0 | F |

Example 12. Hygroscopicity Assessment of Type F

Approximate 10 mg of Type F sample was assessed by hygroscopicity using a dynamic vapor sorption instrument, and tested by XRPD before and after DVS test. The results show that Type F had a water uptake of 1.2% under 80% RH, indicating that Type F is slightly hygroscopic. Type F did not change after DVS test.

Example 13. Solubility of Type A in Water at Room Temperature 10 mg of Type A, B, D, and F samples each was added into a 1.5-mL glass vial, and 1.0 mL of water was then added. The mixture was rolled at 25 rpm at room temperature for 24 hours. The suspension was centrifuged and filtered to isolate the supernatant for HPLC concentration and purity testing and the residual solids were characterized by XRPD. Table 11 shows the summary of solubility assessment of Types A, B, D, and F.

TABLE 11

| Solid Form | Solubility (mg/mL) | pH | Form Change |
|---|---|---|---|
| Type A | 0.013 | 7.4 | Yes, to Type B |
| Type B | 0.006 | 7.7 | No |
| Type D | 0.018 | 8.0 | No |
| Type F | 0.004 | 6.9 | No |

Example 14. Characterization Summary of Type A-F Crystalline Forms

Table 12 shows a summary of the characterization of Type A-F crystalline forms.

TABLE 12

| Crystal Form | Wt. Loss in TGA (%) | Endotherm in DSC (° C., onset) | Form Identity |
|---|---|---|---|
| Type A | 1.8 | 62.7*, 96.6 | Anhydrate |
| Type B | 1.9 | 161.6 | Anhydrate |
| Type C | 11.0 | 127.1 | Solvate |
| Type D | 3.7 | 52.3, 115.6* | Hydrate |
| Type E | NA | NA | Anhydrate |
| Type F | 1.5 | 161.2 | Anhydrate |

*peak temperature.
NA: not available.

Example 15. Interconversion of Type A-F Crystalline Forms

Figure 16:
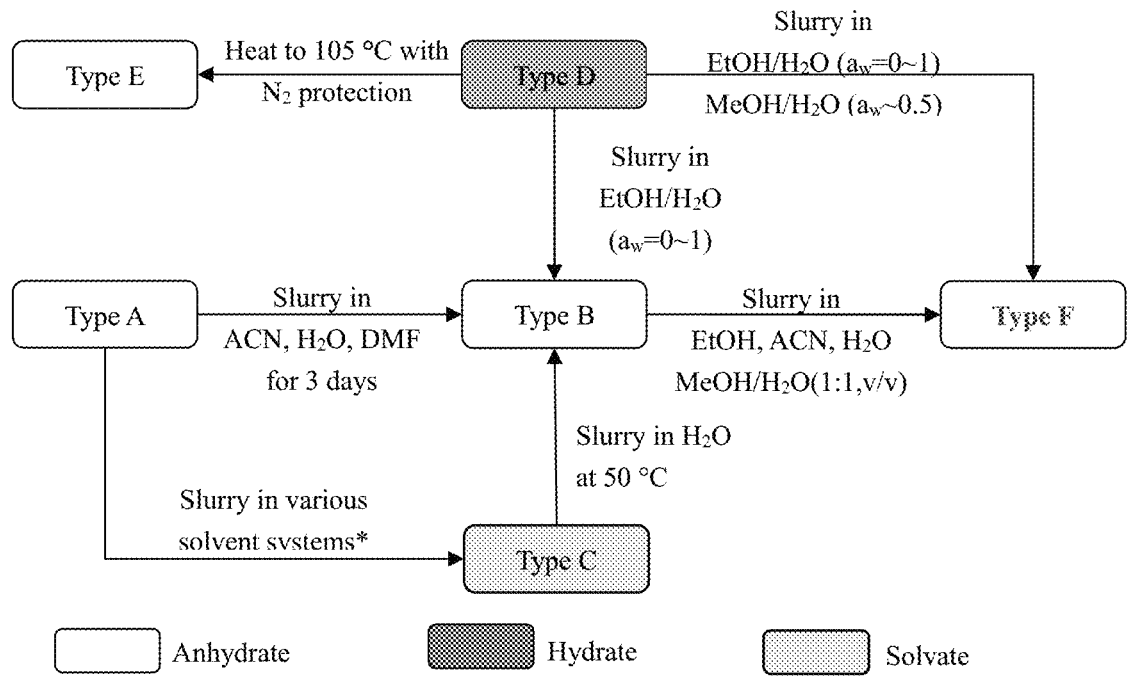
FIG. 16 shows interconversion of Type A-F Crystalline forms.

Relationships among Type A-F crystal forms were investigated via heating and slurry competition experiments. Type A and Type C possess similarity in XRPD patterns and Type C is identified as an isomorphic solvate, which indicate that Type A and Type C may belong to the same crystal family. Hydrate Type D converted to anhydrate Type E after dehydration at elevated temperature and converted to anhydrate Type F after slurry in solvent systems of MeOH/$H_2O$ ($a_w$~0.5) and EtOH/$H_2O$ ($a_w$=0~1) at RT (room temperature, 25±2° C.). Solvate Type C could convert to anhydrate Type B after slurry in $H_2O$ at 50° C. for about 21 days. Anhydrate Type A and B converted to Type F after slurry in ACN, EtOH, MeOH/$H_2O$ (1:1, v/v) and $H_2O$ from RT to 50/70° C. Interconversion relationship is shown in FIG. 16. Overall Type F is the more stable anhydrous form among Type A/B/D/F identified between RT and 50/70° C.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude the specification.

What is claimed is:

1. A crystalline form of 6-(1-acryloylpiperidin-4-yl)-2-(4-phenoxyphenyl)nicotinamide having X-ray diffraction peaks at 5.4°±0.2°, 8.4°±0.2°, 18.7°±0.2°, 19.1°±0.2°, 16.1°±0.2°, 21.9°±0.2°, and 10.1°±0.2° degrees 2θ, and wherein the most intense peak is at 5.4±0.2 degrees 2θ.

2. A crystalline form of 6-(1-acryloylpiperidin-4-yl)-2-(4-phenoxyphenyl)nicotinamide having X-ray diffraction peaks at 16.1°±0.2°, 22.1°±0.2°, 21.6°±0.2°, 8.8°±0.2°, 13.6°±0.2°, and 23.2°±0.2° degrees 2θ, and wherein the most intense peak is at 16.1±0.2 degrees 2θ.

3. A crystalline form of 6-(1-acryloylpiperidin-4-yl)-2-(4-phenoxyphenyl)nicotinamide having X-ray diffraction peaks at 8.4°±0.2°, 5.4°±0.2°, 16.3°±0.2°, 16.1°±0.2°, 18.7°±0.2°, and 21.8°±0.2° degrees 2θ, and wherein the most intense peak is at 8.4±0.2 degrees 2θ.

4. A crystalline form of 6-(1-acryloylpiperidin-4-yl)-2-(4-phenoxyphenyl)nicotinamide having X-ray diffraction peaks at 5.2°±0.2°, 15.0°±0.2°, 3.0°±0.2°, and 18.9°±0.2° degrees 2θ, and wherein the most intense peak is at 5.2±0.2 degrees 2θ.

5. A crystalline form of 6-(1-acryloylpiperidin-4-yl)-2-(4-phenoxyphenyl)nicotinamide having X-ray diffraction peaks at 6.2°±0.2°, 12.4°±0.2°, 18.7°±0.2°, 20.1°±0.2°, and 22.8°±0.2° degrees 2θ, and wherein the most intense peak is at 18.7±0.2 degrees 2θ.

6. A crystalline form of 6-(1-acryloylpiperidin-4-yl)-2-(4-phenoxyphenyl)nicotinamide having X-ray diffraction peaks at 21.4°±0.2°, 20.7°±0.2°, 19.7°±0.2°, 17.7°±0.2°, 15.0°±0.2°, and 16.3°±0.2° degrees 2θ, and wherein the most intense peak is at 21.4±0.2 degrees 2θ.

7. A pharmaceutical composition comprising the crystalline form of any one of claims 1-5 and a pharmaceutically acceptable carrier.

* * * * *